United States Patent [19]

Kronner

[11] 4,089,337

[45] May 16, 1978

[54] UTERINE CATHETER AND MANIPULATOR WITH INFLATABLE SEAL

[75] Inventor: Richard F. Kronner, Roseburg, Oreg.

[73] Assignee: James H. Harris, Roseburg, Oreg.

[21] Appl. No.: 746,418

[22] Filed: Dec. 1, 1976

[51] Int. Cl.² ............................................. A61M 25/00
[52] U.S. Cl. ................................. 128/348; 128/2 A; 128/246; 128/349 B
[58] Field of Search ............................ 128/348–351, 128/344, 325, 241, 245, 246, 2 A, 2 M

[56] References Cited

U.S. PATENT DOCUMENTS

| 397,060 | 1/1889 | Knapp | 128/246 |
|---|---|---|---|
| 559,620 | 5/1896 | Shearer | 128/241 |
| 2,480,041 | 8/1949 | Myller | 128/349 B X |
| 3,896,816 | 7/1975 | Mattler | 128/246 X |
| 3,948,270 | 4/1976 | Hasson | 128/348 |

Primary Examiner—Dalton L. Truluck
Attorney, Agent, or Firm—James D. Givnan, Jr.

[57] ABSTRACT

A flexible catheter having an inflatable member at one end for insertion into a body cavity to seal same against fluid loss. A spring component biases the catheter outwardly of the cavity to assure seating of the inflated member against the cavity wall. A disc abuts a body part to load the spring component during catheter insertion. The disc prevents accidental perforation of the uterus and, with the inflated member affords stability to facilitate uterus manipulation. An air line in the catheter wall admits air to the inflatable member. A stiffener enables the flexible catheter to be used for imparting movement to the body part.

5 Claims, 5 Drawing Figures

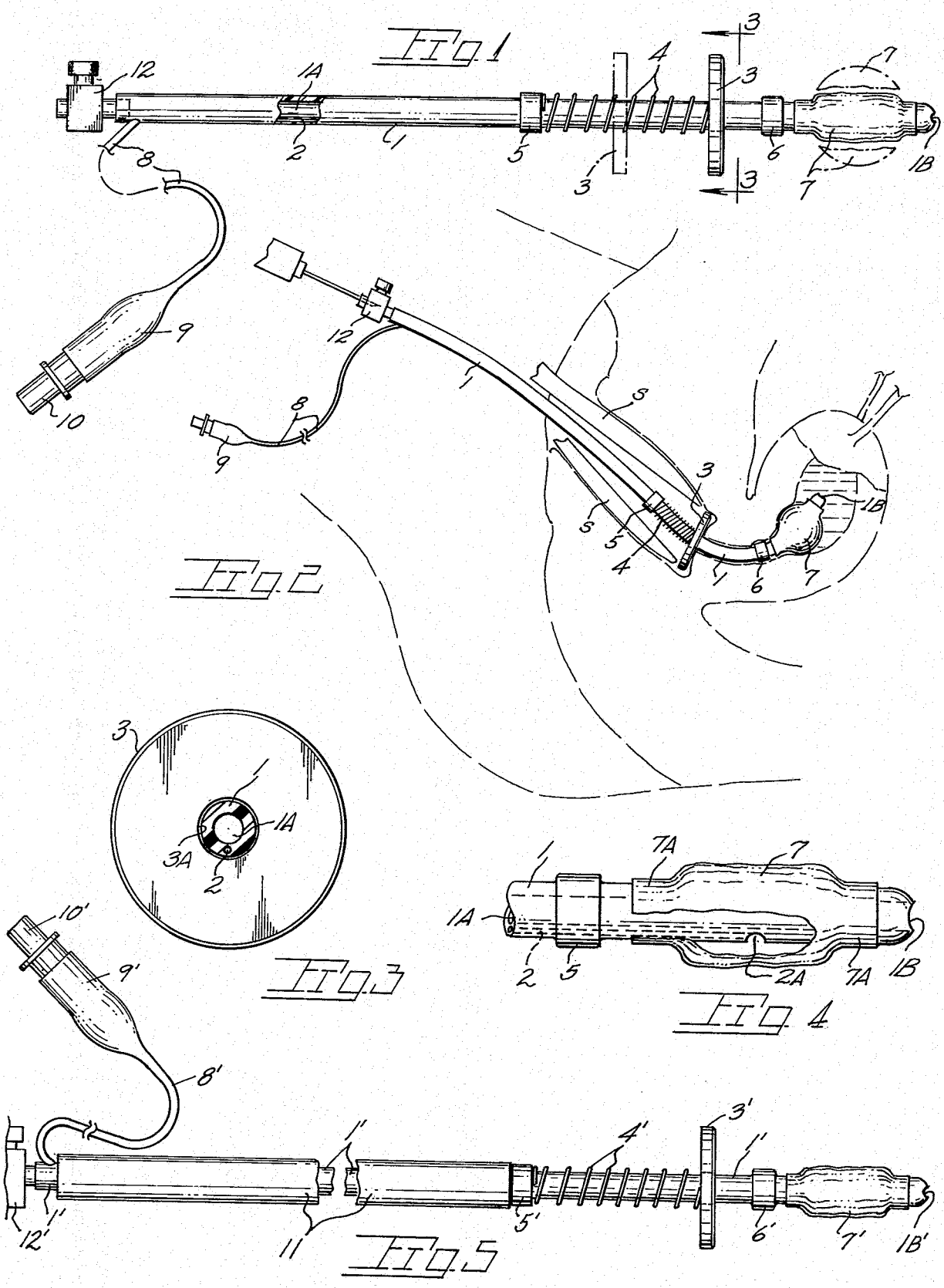

UTERINE CATHETER AND MANIPULATOR WITH INFLATABLE SEAL

BACKGROUND OF THE INVENTION

The present invention relates generally to medical equipment and particularly to a catheter for use in injecting and sealing a fluid within a body cavity such as the uterus and thereafter usable for positioning same.

The prior art encompasses catheters for insertion into different body cavities, as for example, the anal cavity for the purpose of regulating body functions. Additionally, other catheters are intended for insertion into various other cavities both for controlling body functions, as well as for the administration or withdrawl of fluid.

Additionally found in the prior art are catheters in combination with inflatable means provided for the purpose of catheter retention. Examples of prior catheters are found in U.S. Pat. Nos. 2,687,131; 3,459,175; 3,766,920; 3,802,418 and 3,896,816. The prior art also discloses adjustable plates manually positionable along the catheter, in some instances, to prevent fluid expulsion.

SUMMARY OF THE PRESENT INVENTION

The present invention is embodied in a multi-use catheter such uses including the injection of fluid into a cavity such as the uterus, the sealing of the cavity and enabling maniupulation of that portion of the body defining the cavity.

The catheter includes a main tubular member of semi-rigid tubing at the insertable end of which is mounted an inflatable sleeve. Resilient means on said tubular member serves to bias the inflated sleeve in an outward direction seating the sleeve against the body cavity wall to effect a seal. The resilient means assures a positive seal enabling the patient to remain ambulatory without risk of loss of the injected fluid. An air line includes a valve actuated subsequent to maintain sleeve inflation. A stiffener component enables the semi-rigid tubular member of a modified form of the invention to be used to impart movement to that portion of the body defining the cavity.

In one embodiment of the invention a device is provided for the injection of a radio opaque fluid or dye into the uterus and thereafter sealing same for purposes of X-ray visualization.

Important objects of the present invention include: the provision of a device through which fluid may be injected into the uterus at a doctor's office, the vaginal speculum removed and the patient thereafter remaining ambulatory for travel to an X-ray machine with deflating of the inflatable member permitting convenient removal when finished; the provision of a device additionally enabling positioning of internal body parts for remedial purposes or inspection with minimal risk of perforation; the provision of a device which, when inserted into the body cavity, effects a positive fluid tight seal therewith to the extent the patient may be fully mobile as fluid expulsion is prevented by an inflatable member and a cooperating spring biased disc; the provision of a device of economical construction enabling low cost, one time use; the provision of a device able to remain in inserted placement within the body even in the presence of injected fluid pressure within the cavity, and the provision of a device which enables the convenient injection of a dye or other fluid into the uterus and fallopian tubes for inspection purposes.

BRIEF DESCRIPTION OF THE DRAWING

In the accompanying drawing:

FIG. 1 is a side elevational view of the present catheter device;

FIG. 2 is a view of the device operatively disposed;

FIG. 3 is a sectional elevational view taken along line 3—3 of FIG. 1;

FIG. 4 is an enlarged side elevational view of the insertable sleeve end of the device; and, FIG. 5 is a side elevational view of a modified form of the device equipped with stiffener means to enable manual positioning of the uterus.

DETAILED DESCRIPTION OF THE PREFERRED EMBODIMENTS

With continuing attention to drawings wherein applied reference numerals indicate like parts in the following description, the reference numeral 1 indicates a catheter tube of semi-rigid material having a lengthwise extending opening 1A terminating at an orifice 1B. A second or air passageway at 2 (FIG. 4) is formed within the tube wall and is of somewhat lesser length and diameter than the first mentioned passageway. Passageway 2 constitutes a continuation of a later described air line.

A circular disc at 3 is slidably disposed on tube 1 by means of a disc aperture 3A with the aperture being somewhat oversize to permit inclination of the disc to the tube axis for reasons later elaborated. Coacting with said disc is resilient means shown as a helical spring 4 which is confined at its opposite end by stop means 5 fixed in place on tube 1. A collar at 6 confines disc 3 against inward movement. The terms "inner", "inward", "outer" and "outward" are presently used with respect to the device when operatively disposed within a body cavity as viewed in FIG. 2.

An inflatable sleeve is indicated at 7 in sealed, airtight engagement at its ends at 7A with the tube inner end segment. Sleeve inflation is depicted by the broken line position of FIG. 1

An air line is indicated at 8 terminating in communication with air passageway 2 in tube 1 and which passageway ultimately opens into the sleeve interior at 2A in FIG. 4. The outer end of air line 8 is provided with a shut-off valve 9 having a mouthpiece 10. The details of such a valve, other than to say it is operable to close air line 8 after sleeve inflation, are superfluous as such valves are widely known throughout the catheter field.

One embodiment of the catheter is of polyvinyl chloride, semi-rigid tubing approximately 22cm in length and of a diameter to permit entry into the cervix without undue dilation and discomfort. Disc 3 is also of a semi-rigid material such as polyvinyl chloride. The inflatable sleeve may be of any suitable material such as a thin film plastic capable of being inflated to fully occupy and seal the innermost segment of the cervix.

In one use, the device is manually inserted with the aid of a speculum 5 into the cervix after measurement of same with disc 3 coming into yieldable abutment against the end of the cervix. Subsequent inward advancement of the tube 1 results in compression of spring 4 as stop means 5 is advanced thereagainst. With tube 1 so in place and sleeve 7 at least partially in the uterine fundus, the sleeve is inflated via air line 8 and passageway 2. An inward force on tube 1 is thereby applied by such inflation which force is automatically counteracted by spring biased disc 3 resulting in tube 1 being held securely in place. The dye or other fluid, such as a radio opaque fluid, is then injected into the tube passageway 1A for discharge at 1B into the uterus. To prevent fluid escape, a two-way stop cock 12 is fitted to the outer end of tube 1. The fluid may be traced during fluoroscopy to determine the condition of the uterus and fallopian tubes.

A modified form of the invention is shown in FIG. 5 which form is intended to facilitate positioning of the uterus for remedial and inspection purposes with minimal risk of uterus perforation. Parts of the modified form of catheter corresponding to parts of the earlier described catheter are identified by prime reference numerals. An additional component in the modified form of the invention is a tubular section at 11, which is circumposed about tube 1' to provide stiffener means therefor. Tube 1' so reinforced, may impart manual movement to the uterus upon tube manipulation by the physician.

While I have shown but a few embodiments of the present catheter it will be apparent to those skilled in the art that the invention may be embodied still otherwise without departing from the spirit and scope of the invention claimed.

Having thus described the invention what is claimed and desired to be secured under a Letters Patent is:

1. A catheter for insertion into the uterus for sealing same during examination, said catheter comprising,
   a semi-rigid tubular member for uterine insertion through which fluid may be injected, stop means secured to said tubular member for coaction with a resilient member,
   an inflatable sleeve adjacent the insertable end of said tubular member for inflated engagement with the internal uterine opening,
   an air line extending along said tubular member and in communication with said inflatable sleeve for inflating same,
   a disc slidably disposed on the tubular member for uninterrupted limited movement therealong and adapted for initial manually urged abutment with the end of the uterus cervix,
   resilient means on said tubular member and interposed between said disc and said stop means and abutting the latter, and
   said tubular member biased in an outward direction from the uterus by said resilient member acting on said stop means to seat the inflatable sleeve within the internal uterine opening to effect a fluid seal.

2. The catheter claimed in claim 1 wherein said resilient means is a helical spring partially compressed during catheter insertion to inhibit penetration of the tubular member into the uterus.

3. The catheter claimed in claim 1 wherein said air line includes a passageway formed in said tubular member.

4. The catheter claimed in claim 1 additionally including external stiffener means attachable to the exterior of said tubular member outwardly of said stop means to facilitate manipulation of the uterine inserted segment of the tubular member and hence manipulation of the uterus.

5. The catheter claimed in claim 4 wherein said stiffener means comprises a tubular component in telescopic engagement with said tubular member.

* * * * *